United States Patent
Conway

[11] Patent Number: 5,954,511
[45] Date of Patent: Sep. 21, 1999

[54] METHOD FOR TASK EDUCATION INVOLVING MENTAL IMAGING

[76] Inventor: Malcolm J. Conway, 35 Main Rd., Gill, Mass. 01376

[21] Appl. No.: 08/934,099
[22] Filed: Sep. 19, 1997
[51] Int. Cl.[6] .................................................. G09B 19/00
[52] U.S. Cl. ............................................ 434/236; 434/219
[58] Field of Search .................................... 434/236, 238, 434/219, 322

[56] References Cited

U.S. PATENT DOCUMENTS

| | | | |
|---|---|---|---|
| 3,613,266 | 10/1971 | Conway | 434/322 |
| 4,060,915 | 12/1977 | Conway | 434/307 R |
| 4,518,361 | 5/1985 | Conway | 434/307 R |

*Primary Examiner*—Kien T. Nguyen
*Assistant Examiner*—John Edmund Rovnak

[57] ABSTRACT

An improved method of developing and testing the degree of a student's ability to mentally image a task requiring a motor response. Line diagrams symbolizing objects or maps of actions are presented with instructions that invoke mental images of objects and motor response actions. The students ability to respond to the mental image is measured, recorded and shown to the student only after the response is complete.

2 Claims, 7 Drawing Sheets

METHOD FOR TASK EDUCATION INVOLVING MENTAL IMAGING

BACKGROUND

The present invention relates to teaching, learning and testing methods. Specifically, it is an improved method for training students using a process of mental imaging in performing manual tasks. In particular, the process first makes students aware of imaging as a mental action, provides a means for practicing mental imaging combined with a motor skill task performance, and then provides a means for measuring a student's aptitude improvement at performing the mentally imaged task. The present novel improvement involves including reference dots for the practiced mental image and then providing only the reference dots to the students while their aptitude at performing the mentally imaged motor skill task is being measured.

The state of the art is as disclosed by me in previous patents U.S. Pat. No. 3,613,266 issued Oct. 19, 1971, U.S. Pat. No. 4,060,915 issued Dec. 6, 1977, and U.S. Pat. No. 4518,361 issued May 21, 1985. Of particular interest is the 1971 patent entitled "METHOD AND MEANS FOR ENHANCING MENTAL IMAGING CAPABILITIES," wherein I disclose a broad ranging method for training students to mentally image objects and actions without any reference diagrams or feedback in the form of progressive lines or markings. All responses that are measured are made by the student against a blank medium and the responses produce no marks visible to the student such that the progress may be tracked by the student. A record of the action is provided only after the entire exercise is completed.

This prior art has proven to be useful for training students for many tasks and the electronic apparatus added through the disclosures of my other two patents has expanded the automation and basic technology of the field the invention. However, a recent need to train students to mentally imagine an action of a particular amplitude including repeat actions of slightly greater amplitude has shown a need for an improved method which the present invention provides.

SUMMARY OF THE INVENTION

The method of the present invention includes the steps of the student's viewing one or more prepared training diagrams which include dimensional dots arranged at strategic points on the diagram, mentally imaging and practicing a motor response to the training diagrams utilizing said dimensional dots as sizing guides, then with the training diagrams hidden, receiving a display or performance diagram with at a minimum said dimensional dots visible, mental imaging the original training effort and performing the required task without benefit of seeing performance progress while the performance is being recorded and assessed for later review.

The steps of the method and the images used are selected relative to the process to be learned or the purpose of the exercise. When the exercise is for the purpose of studying mental activity as sensed and recorded by MRI (magnetic resonance imaging) equipment or other available means, specifics of the process become most important. Because of possible differences in the way the brain responds to size variations in diagrams being drawn, all people in a study population need to be controlled to respond by drawing diagrams of an identical size and orientation. By giving the student dots placed at corners and intersections of lines of figures to be imaged, the size and orientation will, on average, be the same. To increase complexity and require extra mental imaging effort, the reference dots from several training diagrams are placed together on the display or diagram used for the recorded performance. The student must visualize and select the proper sequence of dots to make a correct response.

The primary object is to provide a method for training students in the performance of motor response tasks that must be mentally imagined first.

A second object is to provide a training method that can be specifically repeated by several students to provide the basis for study of the brain's learning activity.

A further object is to develop and measure a student's mental imaging and recall ability and document improvements therein.

DESCRIPTION OF THE PREFERRED EMBODIMENT

Figure 1:
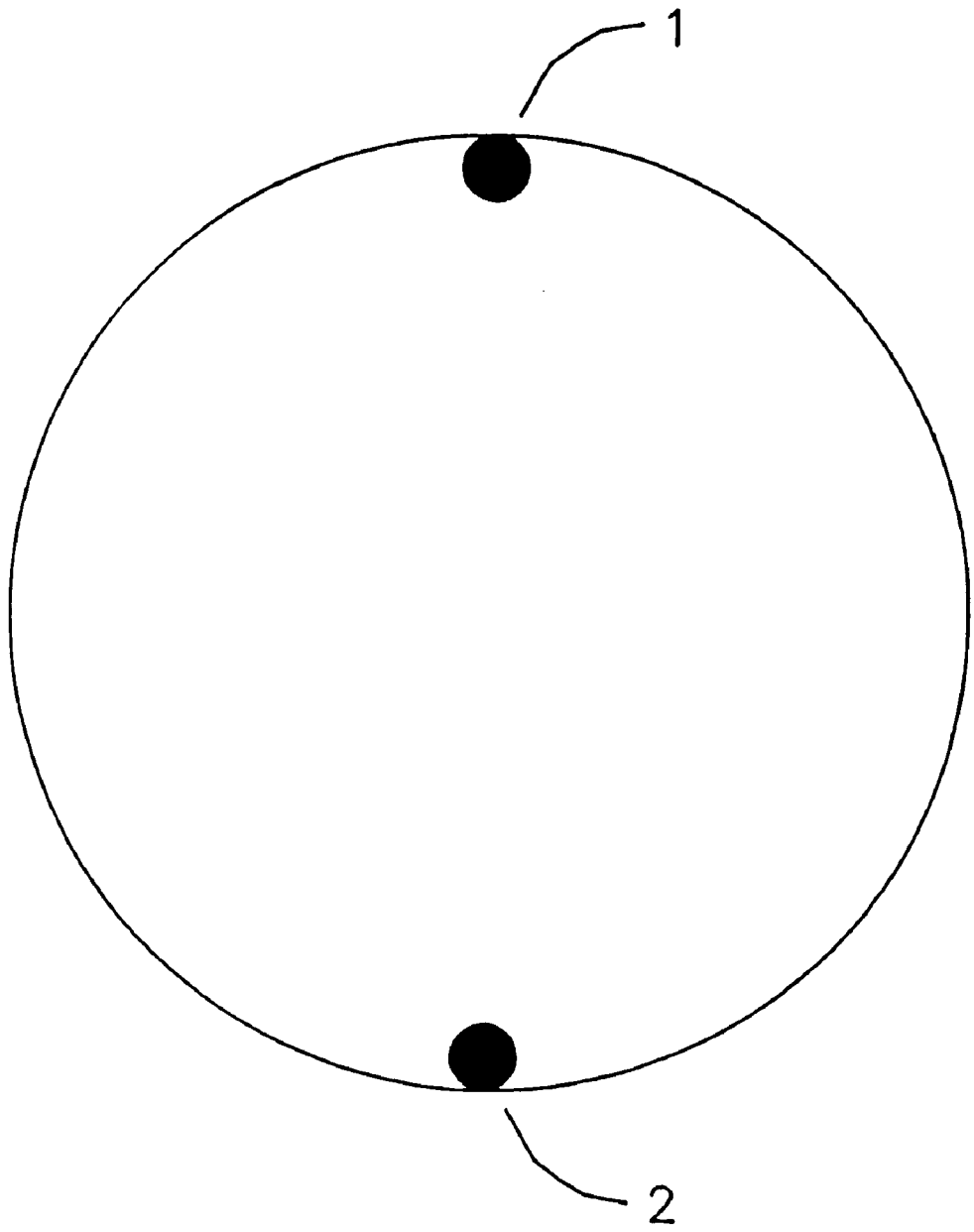
FIGS. 1 through 5 show exemplar first prepared training diagrams.
Figure 2:
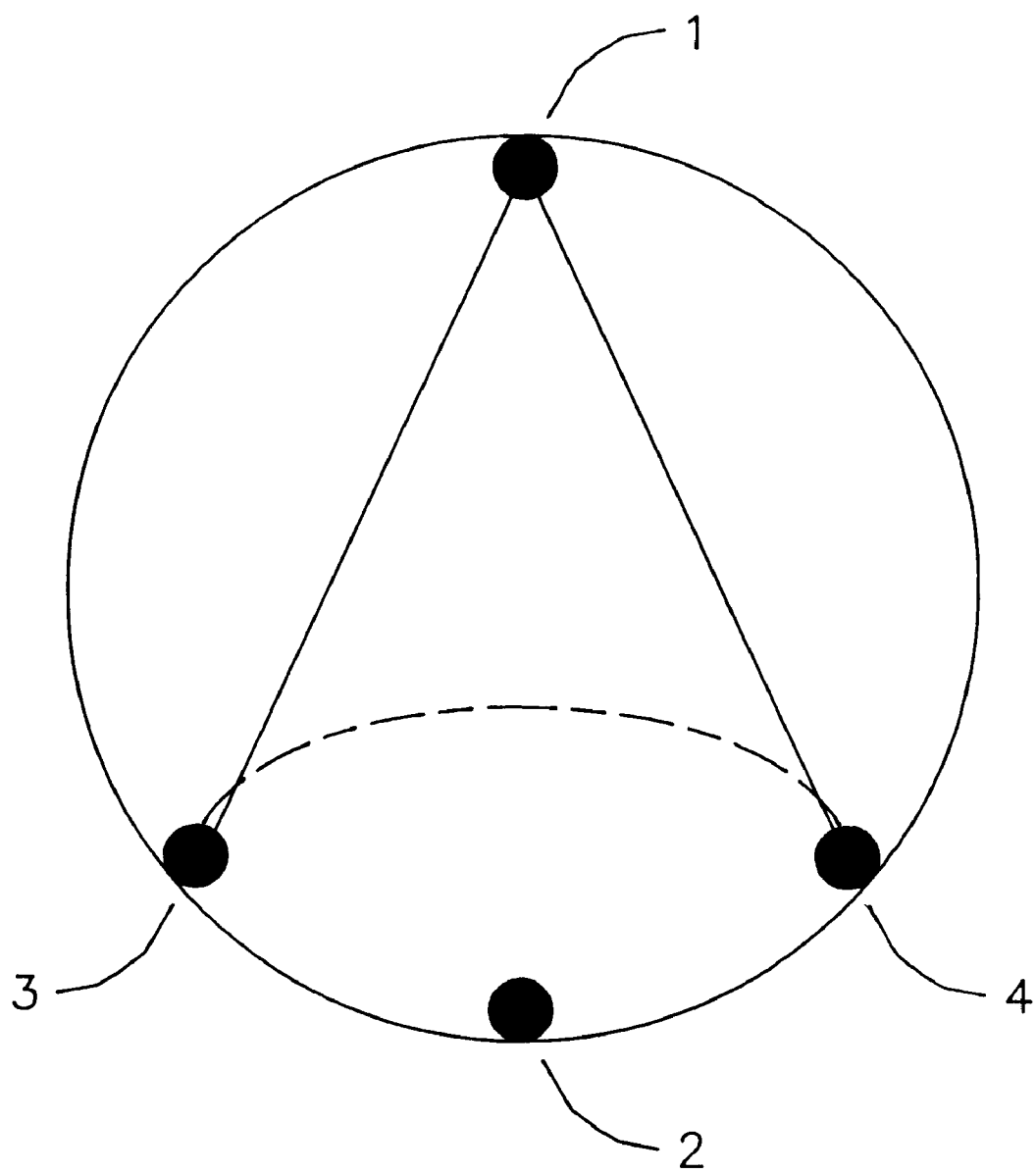

As seen in FIG. 1, a circle training diagram, a circle can be sized by a first dot I and a second dot 2. In FIG. 2 adding a third dot 3 and a fourth dot 4 and connecting them with straight lines to said first dot I and further connecting said third dot 3 to said fourth dot 4 with a curved broken line known to symbolize a hidden line generates a line diagram that can invoke the mental image of a cone within a circle.

Figure 3:
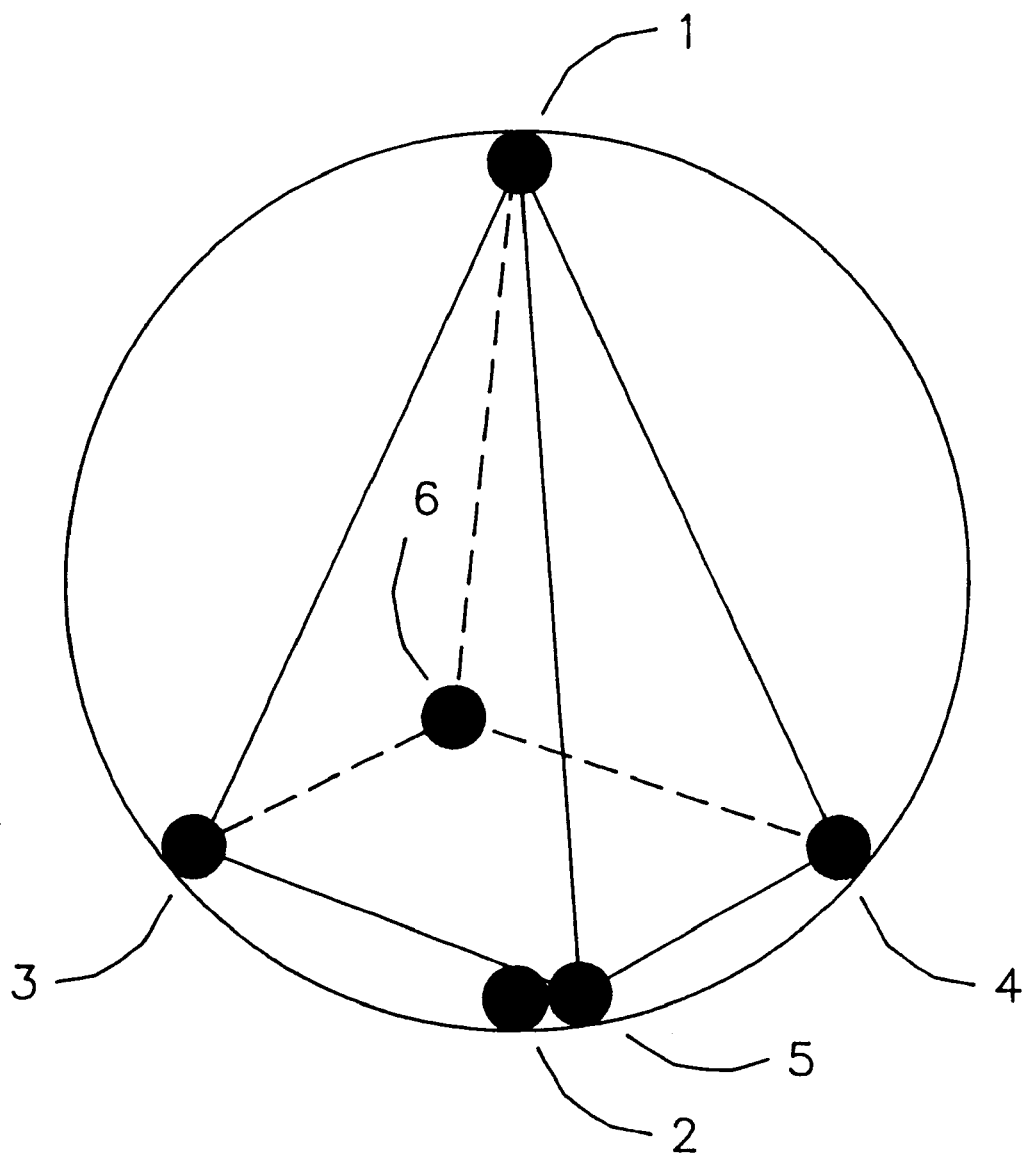
Figure 4:
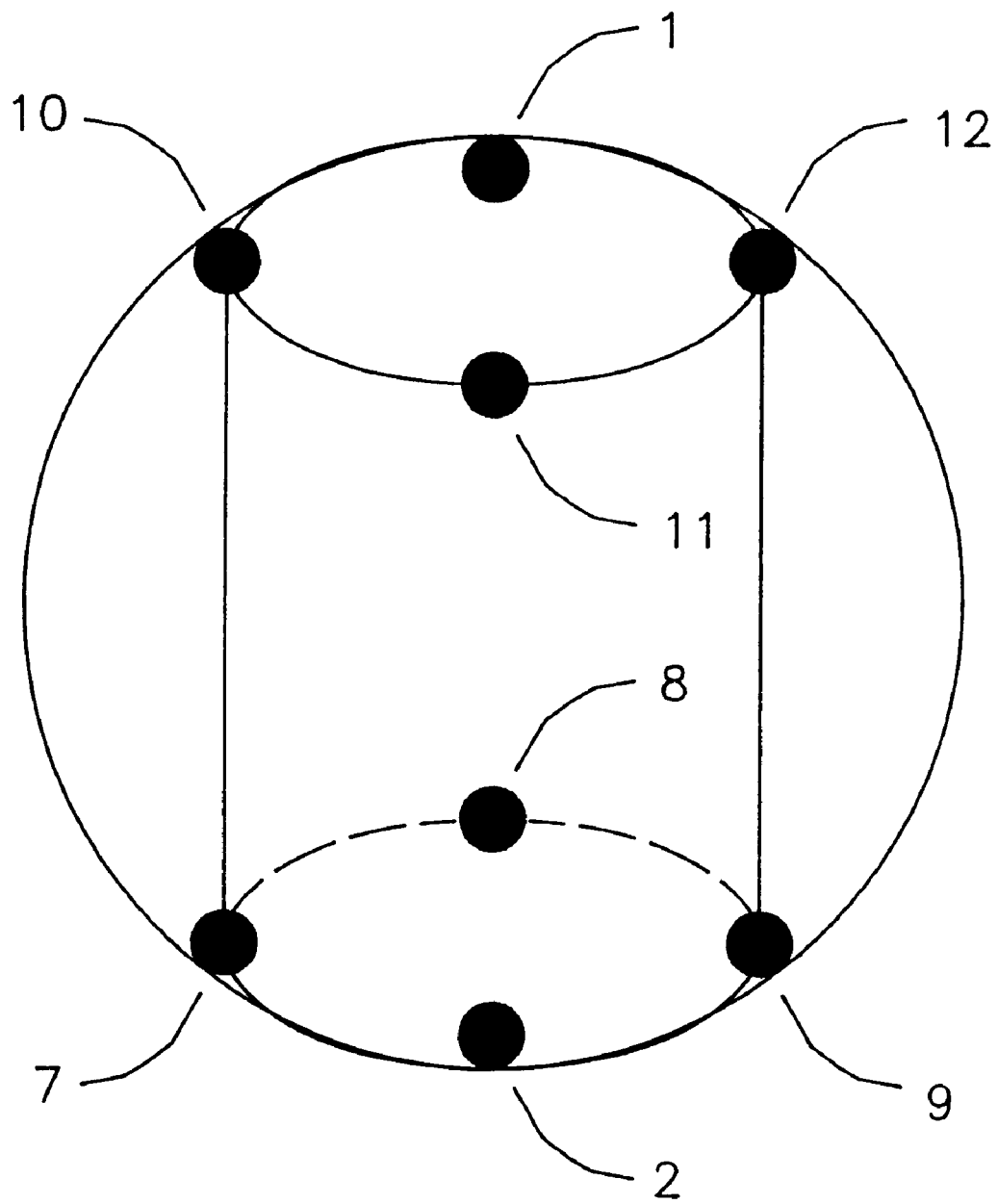
Figure 5:
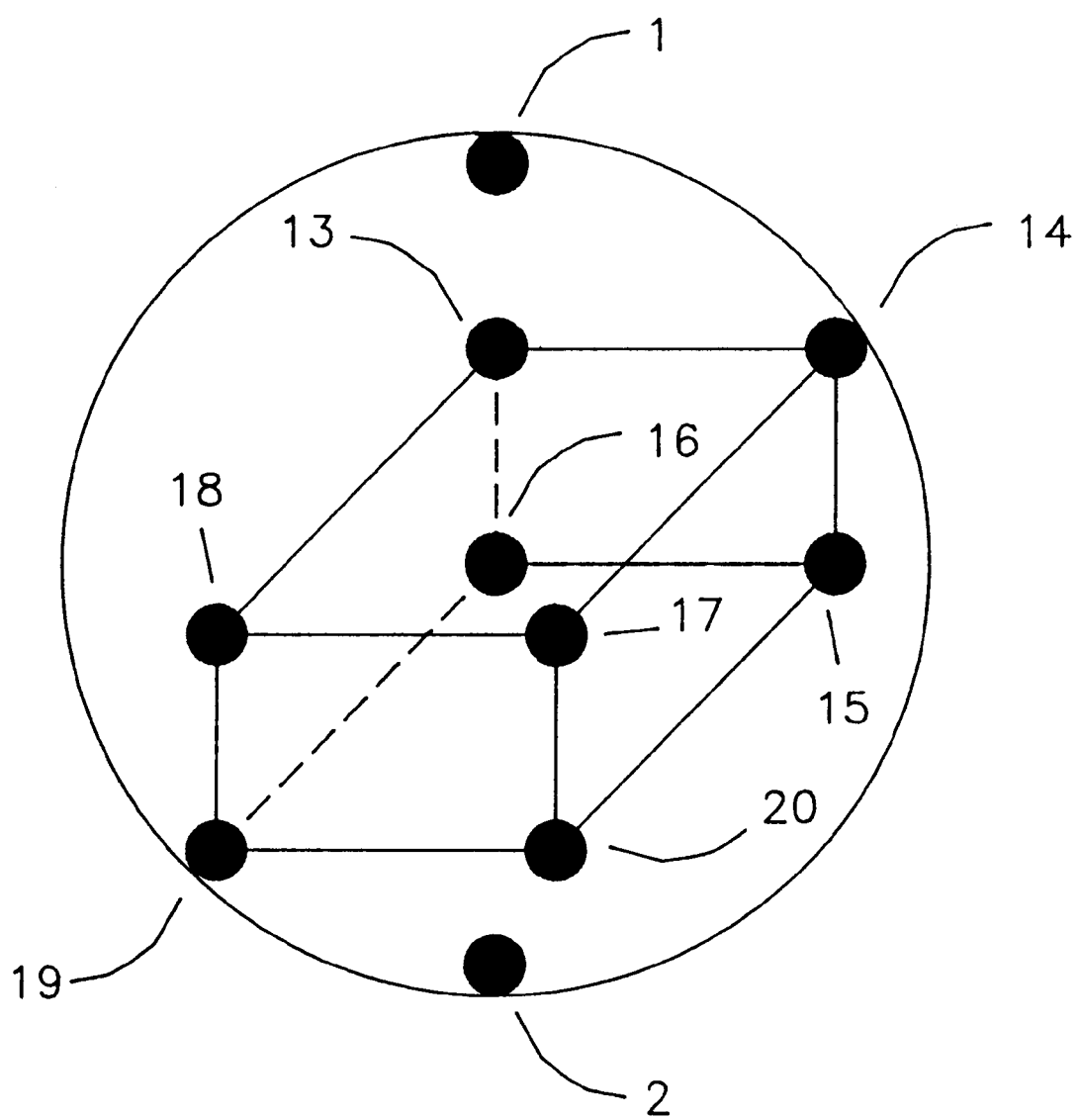

In the same manner in the exemplar training diagram of FIG. 3, a fith dot 5 and a sixth dot 6 are added and connected with straight lines to invoke a mental image of a pyramid within said circle. Now, as in FIG. 4, to make a training diagram that invokes a mental image of a can or tube, only said first dot 1 and second dot 2 are positioned on the diagram to reference the circle. Newly positioned can dots 7 through 12 are added and connected with straight and curved lines. Likewise in FIG. 5, newly positioned box dots 13 through 20 are connected with straight lines to invoke the mental image of a solid rectangle or box.

Once the mental images of objects are recognized, the student must make a mental image or plan of a motor response necessary to complete an assigned task of recreating the diagram that invokes the subject mental image. For example, using the cone diagram of FIG. 2, the student might envision placing a pen or stylus on the first dot 1, moving the pen in a straight line to the forth dot 4, then making a curved line toward the left to the third dot 3, and then finishing by making a straight line back to the first dot 1. As the task difficulty level is increased by including other dots that need to be avoided, the sequence of motor responses to draw the lines might be changed to aid remembering where the proper dots are located.

Figure 6:
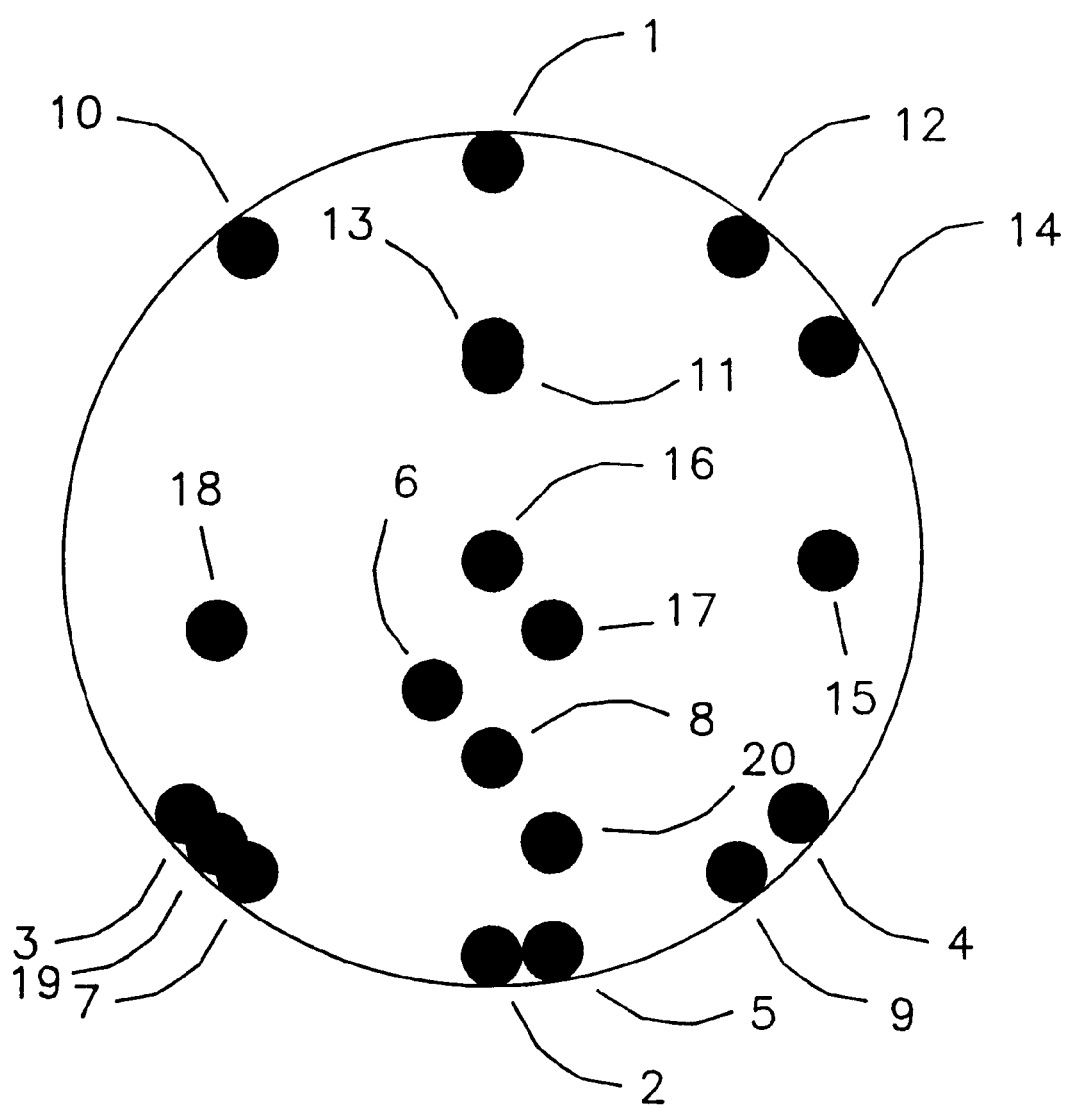
FIG. 6 shows a general matrix of reference dots of the training diagrams.

FIG. 6 is a diagram that might be presented as a practice diagram or a performance diagram. In an actual application, the dots are not numbered, but are placed in the exact relative positions as in the individual training diagrams as was seen in FIGS. 1 through 5. In the example presented here, the student's task might be to draw the lines required to demonstrate that the mental image of a cone, can, pyramid, or box is actually being visualized within the dot pattern. By presenting fewer dots, the level of difficulty is decreased and the mental effort required by the student to accurately form a mental image is significantly reduced. By adding more dots in the performance diagram than are used in the training diagrams (not shown), the difficulty level can be increased and made harder than most minds can handle.

Figure 7:
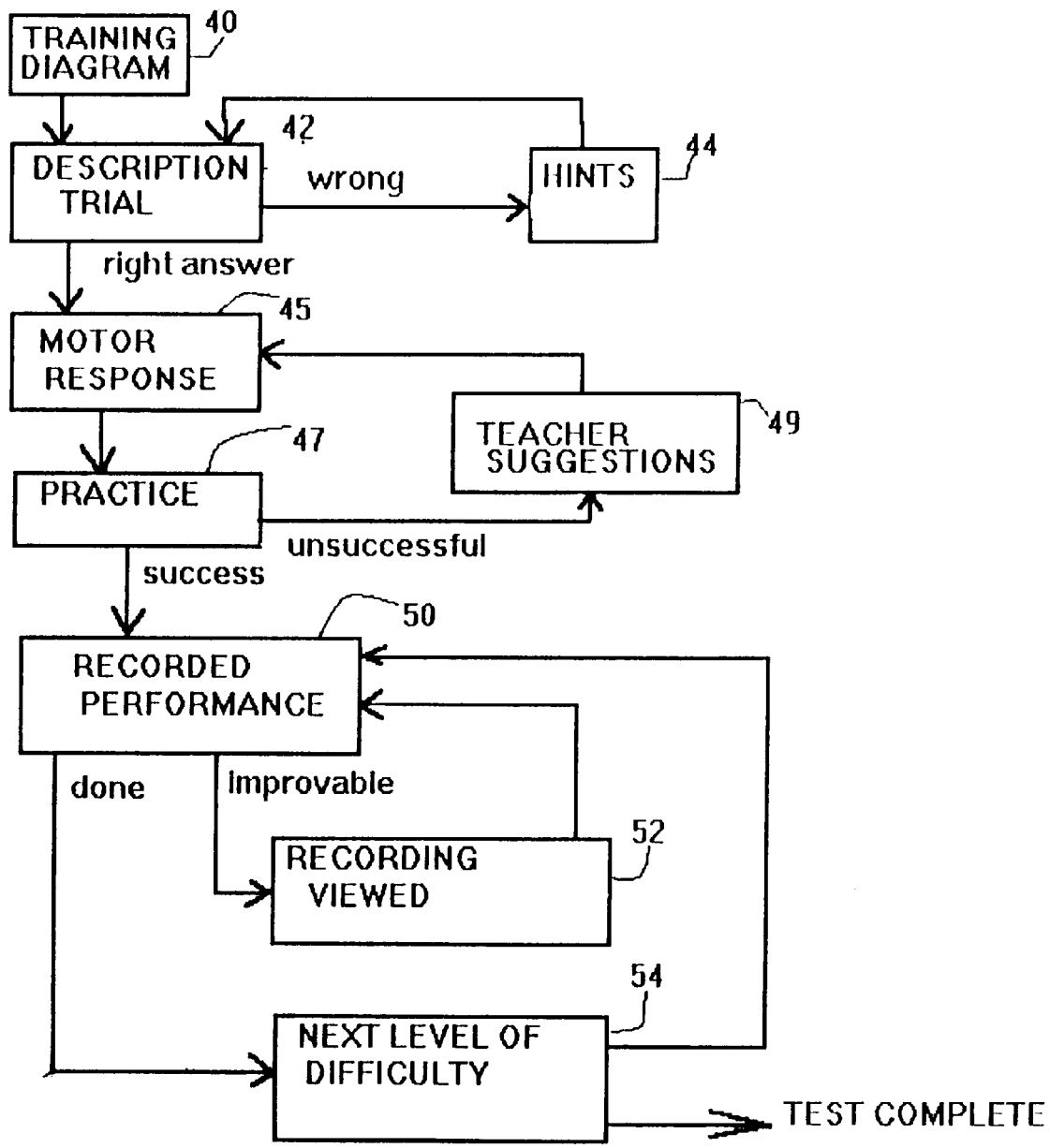
FIG. 7 shows a flow diagram of an exemplar training session using the improvements of the present invention.

FIG. 7 shows a flow chart of an exemplar training session utilizing the basic concept of mental imaging without feedback as disclosed in the 1971 U.S. Pat. No. 3,613,266 with the improvement of the present invention. In a starting step 40, the student is presented a training diagram, complete with reference dots, that is designed to invoke a mental image. Then in a trial step 42, the student is asked to verbally describe the mental image involked by said training diagram. If the student gives a wrong answer, the teacher provides hints, and the student repeats said trial step 42. After the student gives the right answer, the session moves to a motor response step 45 where the student visualizes a sequence of motor responses such as moving fingers or a hand in a particular manner that will move an implement to recreate the diagram. The student then in practice step 47 tries making said sequence of motor responses to recreate the diagram. If unsuccessful the teacher may make suggestions step 49, and the student repeats from the motor response step 45. When the student's practice is a success, the session is ready for a recorded performance step 50 wherein the student is provided a performance diagram that is blank except for reference dots of at least the number presented in said training diagram and placed at precisely the same relative locations as in said training diagram. Said performance diagram may include additional reference dots to increase the difficulty of the mental exercise. Results of the student's motor response are measured and recorded by means disclosed in the aforementioned previous patents or by currently available means provided by personal computer suppliers. The results and any visual feedback of the progress of the motor response are hidden from the student while being tested. If the teacher determines that the student's said motor responses are improveable, the recording viewed step 52 allows the student to see the results and envision motor responses that might improve the results. The recorded performance step 50 is then repeated. When the teacher and student agree that the recorded results probably cannot be improved, the test is done, and a more or less difficult level of performance diagram is presented at step 54, and the test repeats from step 50. When all useful levels of difficulty are complete, the session ends.

It can be understood that the application of the training sessions may be varied by simply changing the training diagrams and the instructions as to what results the test requires.

I claim:

1. A method of developing an individual's capacity to form and utilize accurate mental images of required motor responses to which he has been previously exposed, said method comprising (a) presenting to the individual selected instructional material or training diagrams having a content susceptible of mental visualization of specific motor responses necessary to perform a given test; and (b) Causing the individual to use said motor responses upon a performance diagram to record graphically in a location not visible to the individual a reproduction based on his mental image of said selected material.

2. An improvement of the method of claim 1 wherein (a) said instructional material or training diagrams also comprise first reference dots; and (b) said performance diagram also comprise second reference dots located in at least the same relative positions as said first reference dots.

* * * * *